United States Patent
Pitt et al.

(10) Patent No.: US 7,148,060 B2
(45) Date of Patent: *Dec. 12, 2006

(54) FEEDING TRAY FOR MULTIWELL TEST APPARATUS

(75) Inventors: Aldo Pitt, Wayland, MA (US); Donald Rising, Stow, MA (US); Kenneth DeSilets, Westford, MA (US)

(73) Assignee: Millipore Corporation, Billerica ( * ) Notice: Subject to any disclaimer, the term of this patent is extended or adjusted under 35 U.S.C. 154(b) by 238 days.

This patent is subject to a terminal disclaimer.

(21) Appl. No.: 10/167,023

(22) Filed: Jun. 11, 2002

(65) Prior Publication Data

US 2003/0008387 A1   Jan. 9, 2003

Related U.S. Application Data

(60) Provisional application No. 60/298,240, filed on Jun. 14, 2001.

(51) Int. Cl.
*C12M 1/34* (2006.01)
*C12M 1/12* (2006.01)

(52) U.S. Cl. ............... 435/288.4; 435/297.5; 422/101; 422/102; 73/64.47; 210/321.84

(58) Field of Classification Search ............ 435/288.4, 435/297.2, 297.5, 305.3, 305.2; 422/101, 422/102; 73/38, 64.47; 210/406, 321.84 210/473; 62/291; 220/571
See application file for complete search history.

(56) References Cited

U.S. PATENT DOCUMENTS

| | | | |
|---|---|---|---|
| 3,729,764 A * | 5/1973 | Vines | ................. 15/257.06 |
| 4,307,814 A | 12/1981 | Ihira | |
| 4,427,415 A | 1/1984 | Cleveland | |
| 4,927,604 A | 5/1990 | Mathus et al. | |
| 5,141,718 A | 8/1992 | Clark | |
| 5,326,533 A * | 7/1994 | Lee et al. | ................. 422/101 |
| D359,879 S * | 7/1995 | Fielding et al. | ................ D7/354 |
| 5,462,874 A | 10/1995 | Wolf et al. | |
| 5,650,323 A | 7/1997 | Root | |
| 5,801,055 A | 9/1998 | Henderson | |
| 5,837,198 A | 11/1998 | Itani | |
| 5,972,694 A | 10/1999 | Mathus | |
| 6,131,506 A * | 10/2000 | Kemper | ................. 99/425 |
| 6,471,086 B1 * | 10/2002 | Fleckenstein | ................ 220/570 |
| 7,018,588 B1 * | 3/2006 | DeSilets et al. | ............ 422/101 |
| 2002/0189374 A1* | 12/2002 | DeSilets et al. | .......... 73/864.51 |
| 2002/0192119 A1* | 12/2002 | DeSilets et al. | ............ 422/101 |
| 2002/0192120 A1* | 12/2002 | DeSilets et al. | ............ 422/101 |
| 2002/0192811 A1* | 12/2002 | Pitt et al. | ................. 435/297.5 |

FOREIGN PATENT DOCUMENTS

| | | |
|---|---|---|
| FR | 2 548 685 | 1/1985 |
| JP | 2001141349 A * | 5/2001 |

(Continued)

OTHER PUBLICATIONS

International Search Report dated Jan. 21, 2003.

(Continued)

*Primary Examiner*—William H. Beisner
(74) *Attorney, Agent, or Firm*—Millipore Corporation

(57) ABSTRACT

A feeding tray for retaining a nutrient medium is provided for use with a multiwell filter plate. The feeding tray includes an inclined support surface surrounded by walls that retain nutrient medium on the support surface. The support surface is inclined away from an area for introducing nutrient medium into the feeding tray toward an area for draining the feeding tray of nutrient medium.

10 Claims, 9 Drawing Sheets

FOREIGN PATENT DOCUMENTS

WO     WO 98/35013     8/1998
WO     WO 99/21958     5/1999

OTHER PUBLICATIONS

"Selection of Invasive and Metastatic Subpopulations from a Heterogeneous Human Melanoma Cell Line", BioTechniques, Vo. 9, No. 3 (1990), p. 324.

1. Photograph of top plate of Multi-Screen Dual Access plate prototype, publicly provided by Millipore Corporation in Feb. 1993.

2. Photograph of three piece MultiScreen Dual Access Cell Culture System prototype, publicly provided by Millipore Corporation in Feb. 1993.

* cited by examiner

FEEDING TRAY FOR MULTIWELL TEST APPARATUS

This application claims the benefit of U.S. Provisional Application No. 60/298,240, filed Jun. 14, 2001.

BACKGROUND OF THE INVENTION

This invention relates to a feeding tray for housing a nutrient medium utilized with a multiwell test apparatus suitable for promoting fluid interactions such as by growing cells in a nutrient liquid within a multiplicity of wells. More particularly, this invention relates to such a feeding tray of a multiwell test apparatus which permits adding or removing liquid from the feeding tray of the multiwell test apparatus without disturbing a material in the test multiwell apparatus such as cells within the wells.

At the present time, multiwell test apparatus for testing samples include a multiwell filter plate, a feeding tray, a multiwell receiver plate and a lid. The wells of the multiwell filter plate are formed of a tubular member with an open end to which is attached a membrane such as a microporous membrane. The tubular members can be inserted into a feeding tray containing a nutrient medium so that cells in the wells can be attached to the membrane and grown thereon. The cells are fed as nutrients pass from the nutrient medium through the membrane and to the cells at a rate controlled by the concentration gradient of nutrients from the medium to the cells. The nutrient medium in the feed tray is periodically replenished to maintain cell growth. It is desirable to effect replenishment of the nutrient medium quickly and in a manner that avoids damage to the membranes and the cells.

After the desired level of cell growth on the membranes of the wells has been attained, the multiwell filter plate can be utilized in conventional assay methods. These assay methods generally are effected by positioning the membranes and cells on the multiwell filter plate into the wells of the multiwell receiver plate, such as a 96 well receiver plate positioned below the multiwell filter plate or a receiver plate that has the same number of wells in register with the cell/filter plate. The wells of the multiwell receiver plate contain a liquid composition to be assayed. The composition to be assayed diffuses into the cells and then through the membrane. The resultant liquid products within the wells of the multiwell filter plate or in the wells of the multiwell receiver plate then are assayed to determine the capability of the composition being assayed to permeate the cell barrier.

After the cells have been satisfactorily grown and the feeding tray is to be replaced by the multiwell receiver plate, it is desirable to minimize transport of the nutrient medium to the multiwell receiver plate thereby to minimize dilution of the composition being assayed. Thus, it is desirable to remove any droplets of nutrient medium retained on the lower surfaces of the membranes after the multiwell filter plate is removed from the nutrient medium in the feeding tray.

An important component in the drug discovery and development process is the determination of the oral absorption and bioavailability of new compounds. In order to perform this evaluation in a cost effective, high throughput and sensitive assay, it is ideal to use an in vitro device with a multitude of wells containing cells, a small amount of assay material and automation. Classically, the determination of in vitro oral absorption characteristics is performed using a defined epithelium cell line and measuring the apparent transport rate of the drug across a monolayer of the cells. More recently it is possible to rank/order the passive transport rate of potential drug candidates using an artificial membrane barrier. The values generated from these in vitro experiments are valuable methods for screening the most likely successful drug candidates long before the oral absorption rate are validated by in vivo measurements. A typical experiment for determining the drug absorption characteristics of a known or unknown chemical compound is performed as follows. The multiwell device is seeded with epithelium cells on top of the filter in a defined nutrients medium. The same medium is also added to the single well feeding tray located below and in fluid contact with the device containing the cells. The cells are allowed to proliferate and differentiate over a number of days. The nutrient medium is periodically replaced with fresh medium to replenish exhausted nutrients and remove waste and dead cells. At the end of a growing time, the cells and multiwell device are gently washed with an isotonic buffer to remove protein and residual nutrient medium. At this time, the multiwell filter plate is transferred to the multiwell receiver plate and the chemicals to be assayed are introduced to either the compartment above the cell layer or below the cells and filter support in the multiwell receiver tray. The opposing chamber is filled with drug free buffer and the multiwell device is incubated for some period of time, typically at 37 degrees Centigrade with shaking. If multiple time points are desired, sampling from either compartment can be achieved without separating the device. The amount of drug/chemical that is transported across the cell barrier can be determined by a variety of analytical methods, but typically is determined using LC/MS/MS (Liquid Chromatography/Mass Spectroscopy/Mass Spectroscopy).

Accordingly, it would be desirable to provide a feeding tray that facilitates replenishing the nutrient medium in a feeding tray quickly and in a manner which preserves the integrity of the membranes and cells on the membrane.

SUMMARY OF THE INVENTION

This invention will be described herein with reference to the growing and use of cells on a membrane positioned and secured to the bottom of each of a multiplicity of wells. However, it is to be understood that the present invention need not be used in conjunction with cells. Other representative uses include filtration, dialysis, or the like.

The present invention provides a feeding tray for retaining a nutrient medium, which can be a liquid or a gel, for use in a multiwell test apparatus. The feeding tray promotes quick replenishment of the nutrient medium while avoiding damage to membranes secured to a multiplicity of wells or damage to cells positioned on the membranes. The feeding tray comprises an inclined bottom surface for the nutrient medium surrounded by walls that retain the nutrient medium on the inclined bottom surface. The bottom surface is inclined so that the nutrient medium can be supplied to the feeding tray at a high point of the inclined bottom surface and so that the nutrient medium can be removed from the bottom surface at a low point of the inclined support surface. By providing such a feeding tray, the nutrient medium can be supplied to the feeding tray in a manner that assures determining when spent nutrient medium is substantially completely removed from the feeding tray. The feeding tray also allows for both adding and removing the nutrient medium at the same time.

In one embodiment, the feeding tray includes a plurality of protrusions such as posts secured to and extending from the bottom surface, one or more protrusion positioned adjacent each well which extends into the feeding tray. The protrusions displace some of the volume of nutrient medium, thereby reducing the amount of nutrient medium needed to fill the feeding tray to the desired level. A guide means is provided for positioning the wells to contact a protrusion when they are removed from the feeding tray so that any liquid droplet extending from the bottom surface of the membrane is guided by the protrusion back into the feeding tray. Thus, the protrusion provides a means for removing excess liquid from the membrane that would dilute a liquid solution in the wells of a multiwell receiver plate subsequently utilized in conjunction with the multiwell filter plate.

In another embodiment, the use of one or more baffles, either formed as part of the bottom of the feed tray or formed separately and freely sitting in the feed tray may be used to control the movement or sloshing of the liquid in the tray during handling.

DESCRIPTION OF SPECIFIC EMBODIMENTS

While the present invention is described with reference to effecting cell growth in a multiplicity of wells, it is to be understood that the present invention is applicable to manipulations involving access areas for introducing or removing liquid to effect desired processing, for example dialysis or diffusional separation while avoiding movement of membranes in the wells.

Figure 1:
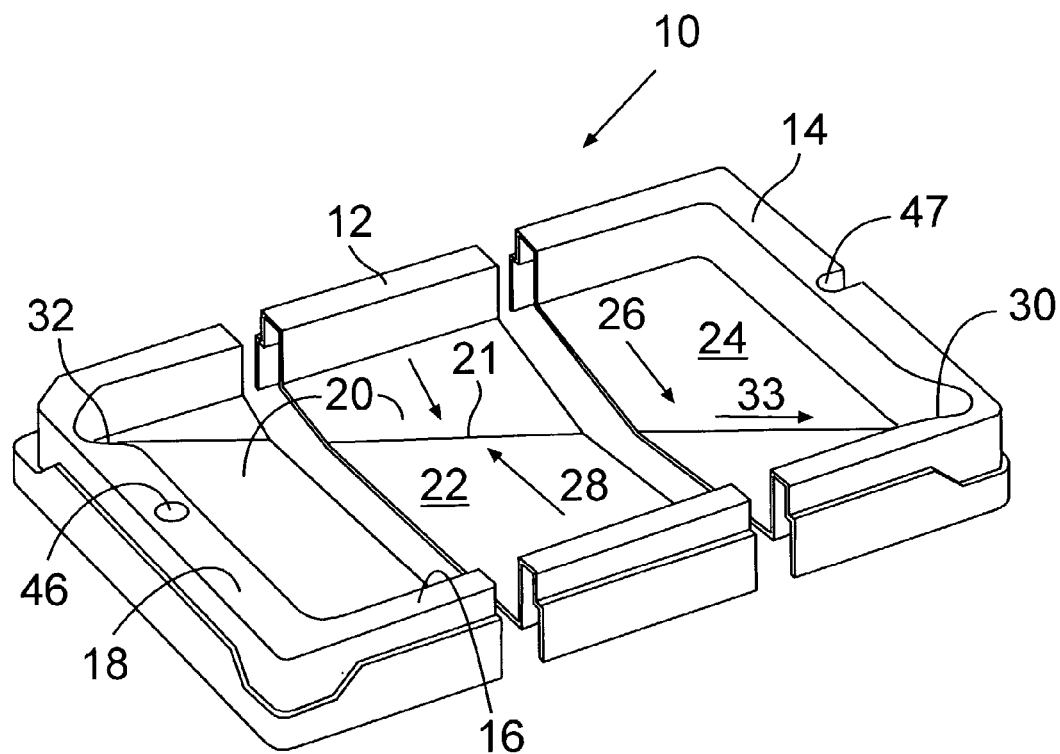
FIG. 1 is a top perspective view of the feeding tray of this invention.

Referring to FIGS. 1 and 2, the feeding tray 10 of this invention includes walls 12, 14, 16 and 18 and bottom surface 20 to house a liquid or gel nutrient medium. The bottom surface 20 includes two surface subsections 22 and 24 separated by drain path 21. The surface subsections 22 and 24 are inclined downwardly from walls 16 and 12 in the direction exemplified by arrows 28 and 26 toward drain path 21. Drain path 21 provides fluid flow from liquid introduction area 32 on surface 20 to liquid drain area 30 as exemplified by arrow 33. A method for introducing and removing liquid from feeding tray 10 will be described more specifically below with reference to FIG. 3A. Feeding tray 10 also is provided with recesses 46 and 47 in FIG. 1 which will be described more specifically below with reference to FIG. 3A.

Figure 2A:
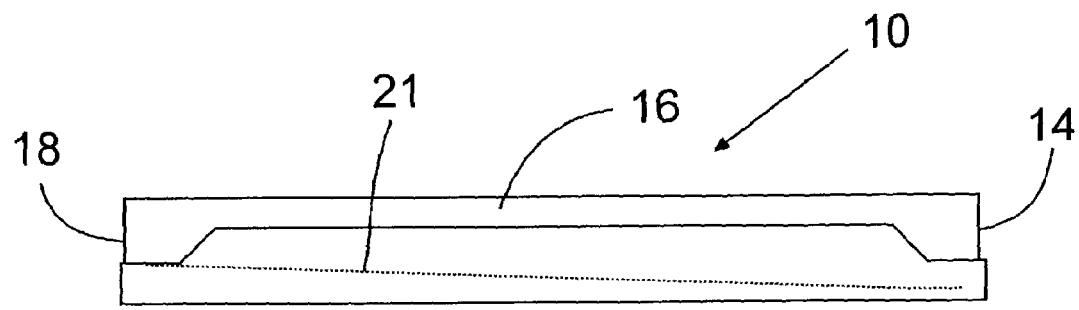
FIG. 2A is a side view of the feeding tray of FIG. 1.

It is to be understood that while the bottom surface of FIGS. 1 and 2A is the preferred configuration of this invention, any inclined surface which directs liquid from a liquid introduction area to a liquid drainage area of the support surface can be utilized.

Figure 2B:
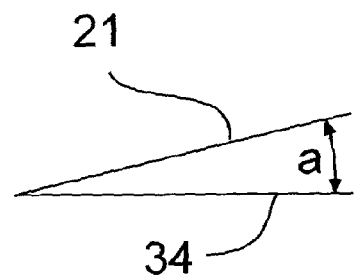
FIG. 2B illustrates the inclined angle of a surface of the feeding tray of this invention.

Referring to FIG. 2B, the angle of incline, a, of drain path 21 to the horizontal 34 may vary from place to place and is typically between about 20 degrees near liquid introduction area 32 and about horizontal near liquid drain area 30, preferably between about 5 degrees and about horizontal, although drain path 21 could have the same angle, a, throughout its length. While the angle, a, can be greater than 20 degrees, it is not desirable since volumes of nutrient medium larger than necessary would be required to submerge the membranes 43 (FIG. 3B) of the multiwell filter plate 40. Surface subsections 22 and 24 may intersect the surrounding walls 12, 14, 16 and 18 at any height, but preferably intersect the walls at a common height so that the intersections lie in a horizontal plane. The angle of the incline, a, of surface subsections 22 and 24 will necessarily vary depending on the local depth of the drain path 21 and the distance from a wall to the drain path 21, but typically is at least 2 degrees and preferably at least 5 degrees. In addition, an angle, a, less than 2 degrees would unnecessarily increase drainage time of nutrient medium from the feeding tray 10.

Figure 3A:
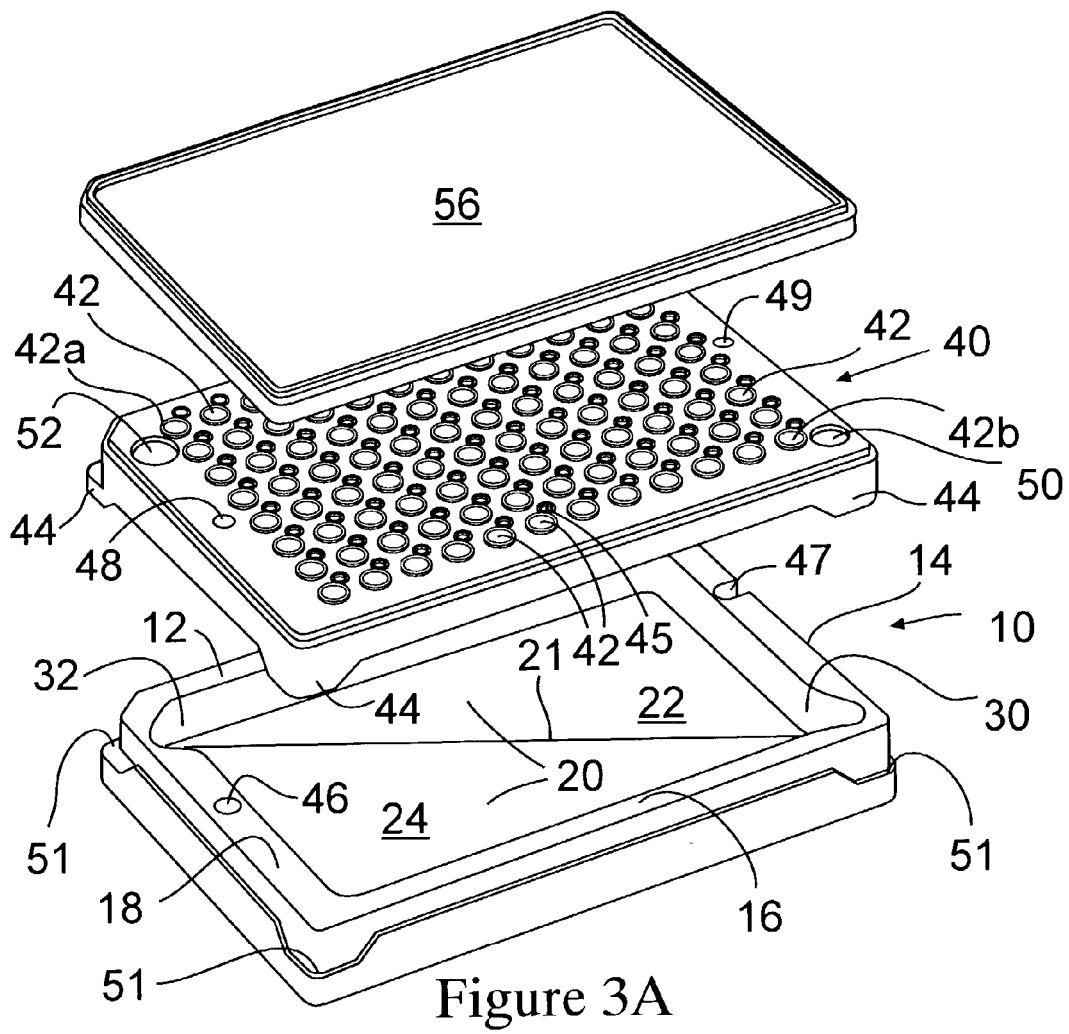
FIG. 3A is a top exploded view of a multiwell test apparatus utilizing the feeding tray of this invention.
Figure 3B:
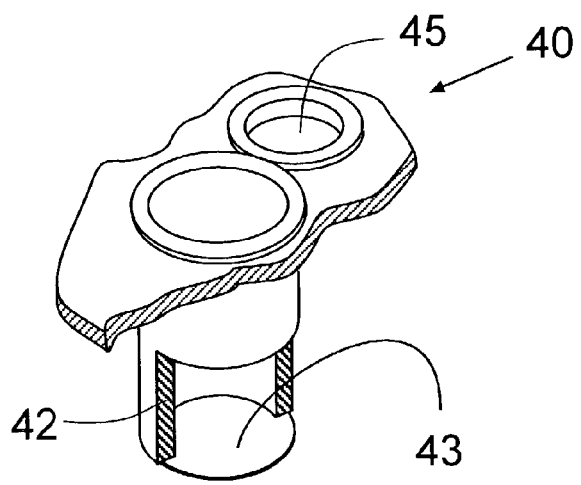
FIG. 3B is a partial cross-sectional view of a well and access hole of the multiwell test apparatus of FIG. 3A.

The use of feeding tray 10 is exemplified with reference to FIGS. 3A and 3B. As shown in FIGS. 3A and 3B, the feeding tray 10 is positioned below a multiwell filter plate 40 which includes a multiplicity of wells 42, such as 96 wells. Different multiplicities of wells may be used as desired, such as 6, 8, 24 or 384 wells that are commonly used in the industry today for various tests. A porous membrane 43 is secured to the bottom of each of the wells 42. Alternatively, as is well known in the art a single sheet of membrane may be sealed across the bottom the plate and the areas outside of the wells are rendered non-porous, covered such as by an injection molded plastic bottom layer or are removed. In use, the feeding tray 10 is provided with a depth of nutrient medium such that the membranes 43 of the wells 42 are immersed in the nutrient medium. Each of the wells 42 has associated therewith an access hole 45 that permits access to a well of a multiwell receiver plate (not shown) which replaces the feeding tray during a subsequent sample assay step. The multiwell receiver plate (not shown) is provided with the same number of wells as the number of wells 42 in the multiwell filter plate 40. The wells of the multiwell receiver plate are shaped to accommodate the wells 42 of the multiwell filter plate 40 and a syringe, cannula, pipette or the like which extends through access holes 45 of the multiwell filter plate 40.

The multiwell filter plate 40 can be provided with four legs 44 that fit into recesses 51 of feeding tray 10 thereby to provide mechanical stability of multiwell filter plate 40. The legs 44 also serve to position the membranes 43 at the bottom of wells 42 to avoid contact with bottom surface 20 thereby to promote contact of liquid with the membrane 43. Feeding tray 10 also is provided with recesses 46 and 47 into which posts 48 and 49 fit. The posts 48 and 49 are asymmetrically positioned on feeding tray 10 so that well 42a is always positioned at the top left position of the well array and so that well 42b is always positioned at the lower right position of the well array. This position assures that a well always can be correctly identified according to its position. The posts 48 and 49 also position wells 42 of multiwell filter plate 40 at desired positions. The nutrient medium can be replenished through opening 52 in multiwell filter plate 40. Nutrient medium can be drained from feeding tray 10 through opening 50. Replenishment and drainage can be effected with a liquid handling device such as a syringe, a cannula, pipette or the like. Since drainage area 30 is positioned at the lowest point of surface 20, complete drainage can be easily effected. Alternatively, drainage and replenishment can be effected simultaneously without the need to move multiwell filter plate 40 relative to feeding tray 10 or tipping the entire multiwell test apparatus. It is to be understood that nutrient medium can be both introduced to and removed from feeding tray 10 through opening 50 without need for opening 52. However, use of opening 52 allows simultaneous drainage and replenishment. Removable lid 56 is utilized to maintain sterility within wells 42 and to minimize evaporation of the nutrient medium.

Figure 4:
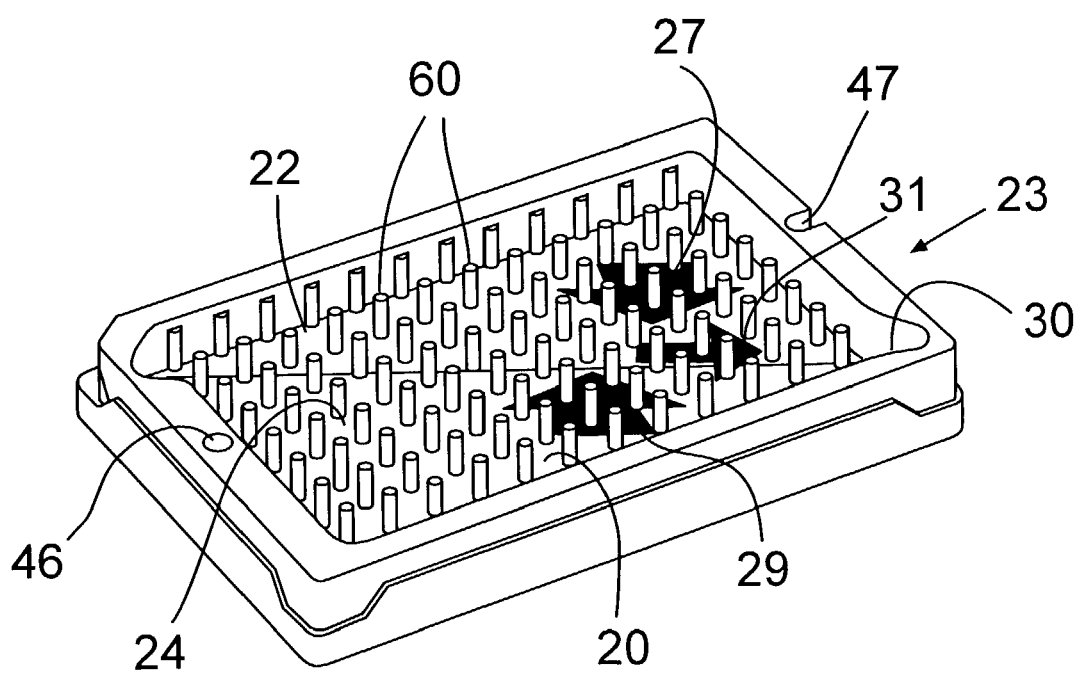
FIG. 4 is a perspective view of an alternative embodiment of the feeding tray of this invention.

Referring to FIG. 4, an alternative feeding tray 23 of this invention is illustrated. This embodiment is provided with posts 60 extending from the inner and supporting surface of the feeding tray 23 between and beside the wells of the multiwell filter plate. As shown, posts 60 extend from surface 20 to a position where they can displace nutrient medium from between wells 42. The purpose of this displacement is to reduce the amount of nutrient medium needed to fill the feeding tray 23 to the desired levels. The feeding tray 23 also comprises inclined surfaces 22 and 24 that effect liquid flow in the directions of arrows 27 and 29 and in the direction of arrow 31 into the drainage area 30.

Figure 5:
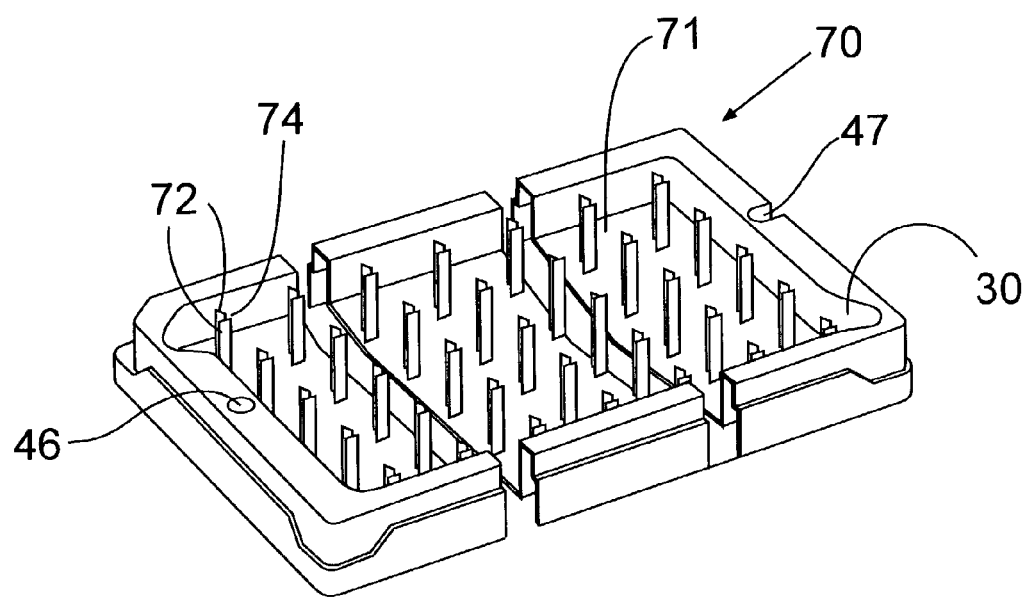
FIG. 5 is a perspective view of an alternative feeding tray embodiment of this invention.

Referring to FIG. 5, the posts 60 of the feeding tray of FIG. 4 are replaced in feeding tray 70 with guide wall protrusions 72 which are positioned to displace liquid between the wells 42 in the manner set forth above with reference to FIG. 4. The protrusions 72 include openings 74 that direct liquid to drainage area 30 from which liquid can be removed with a conventional syringe, cannula, pipette or the like. The bottom surface 71 also is inclined in the same manner shown in FIG. 3A.

Figure 6:
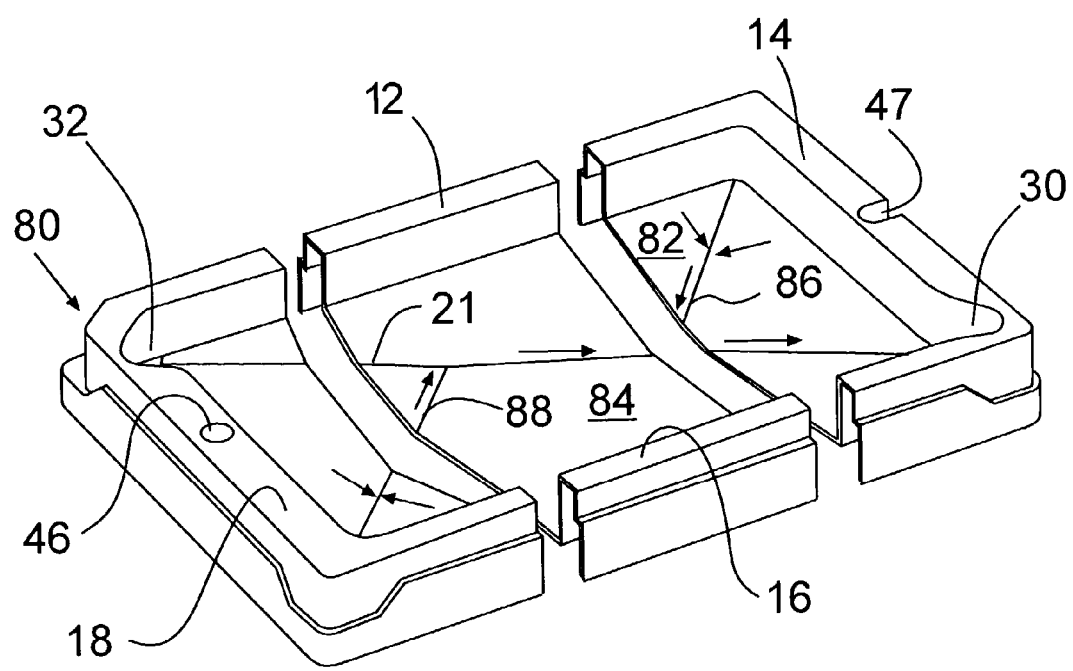
FIG. 6 is a perspective view of an alternative tray of this invention.

Referring to FIG. 6, the feeding tray 80 is provided with walls 12, 14, 16 and 18 as well as a drain path 21. Surface sections 82 and 84 are provided with pathways 86 and 88 that are positioned below surface sections 82 and 84 to provide drainage of nutrient medium to drain path 21 and then to liquid drain area 30.

In an alternative embodiment, the feed tray can have a single inclined bottom surface that is inclined from wall 18 toward wall 14 and drainage area 30.

Figure 7:
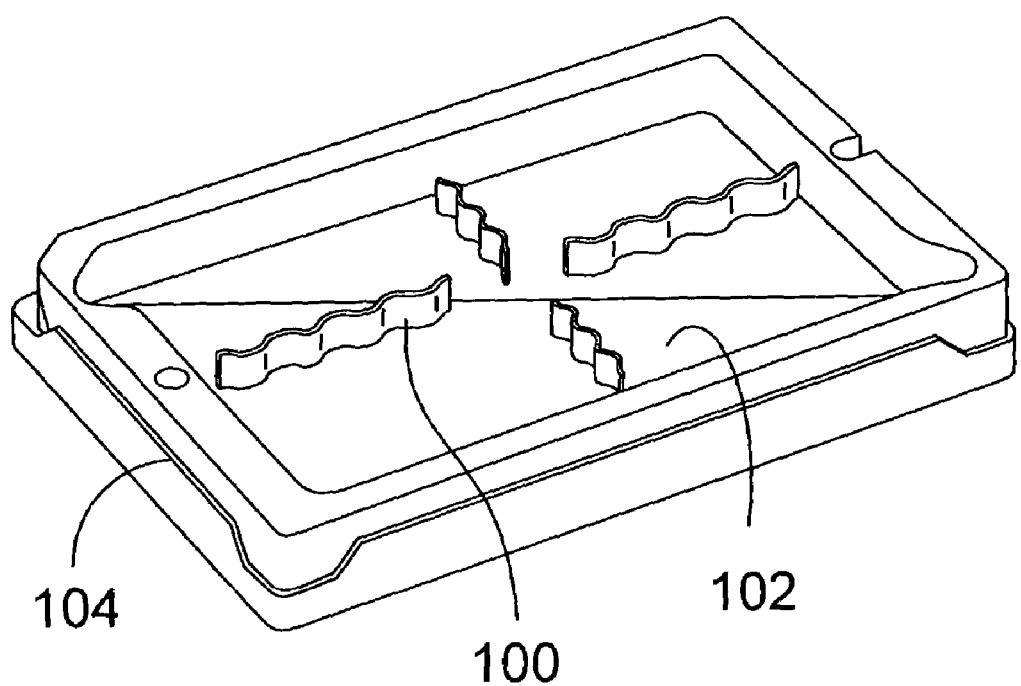
FIG. 7 is a perspective view of an alternative feeding tray embodiment of this invention.

In a further alternative embodiment of the present invention, one may use one or more baffles to reduce the movement or sloshing of the liquid in the feed tray, especially during handling, by humans or robotic equipment. FIG. 7 shows one such embodiment.

In this embodiment, the use of four baffles 100 is shown. The baffles 100 are attached to the bottom 102 of the feed tray 104. Preferably they are formed as part of the feed tray 104 such as by injection molding along with the tray when it is made although they may added as a separate element that is either attached to the tray sides or bottom or allowed to rest freely on the bottom of the tray. As shown, the baffles are arranged in a cross-like pattern and are separate and distinct from each other. As shown, they are also each formed in a repetitive "S" or wavy pattern. Alternatively, the baffle(s) 100 may be straight or curvilinear or crossed (X-like elements) or the like so long as they are able to perform their function while allowing the multiwell filter plate (not shown) to fit into the feed tray 104 and to allow the fluid in the feed tray 104 to flow so that no dead spots occur. As shown, the baffle(s) 100 do not touch the sidewalls of the tray 104. They may if desired. Preferably when they do touch the sidewalls, there are one or more through holes formed in the baffle, preferably along its lower edge to allow for unimpeded fluid movement along the walls.

The height of the one or more baffles 100 is not critical so long as it is sufficient to help reduce the amount of movement of the liquid in the feed tray 104 while being handled. Typically, one can have the baffle height between 20% and 100% of the depth of the liquid in the tray 104. In another embodiment the baffle(s) height is between 35% and 80% of the depth of the liquid in the tray 104. Alternatively, the baffle(s) height is between 50% and 75% of the depth of the liquid in the tray 104.

The number of baffles is not critical. In one embodiment, it is preferred that only one baffle, either running at least partially the length or the width of the tray be used. In another embodiment, it is preferred that at least two baffles, at some defined cross direction to each other, be used. In such an embodiment, the two baffle(s) may be from about 25 degrees to 90 degrees to the direction of the other so as to ensure that the liquid movement is controlled in both the tray length and tray width directions.

Figure 8A:
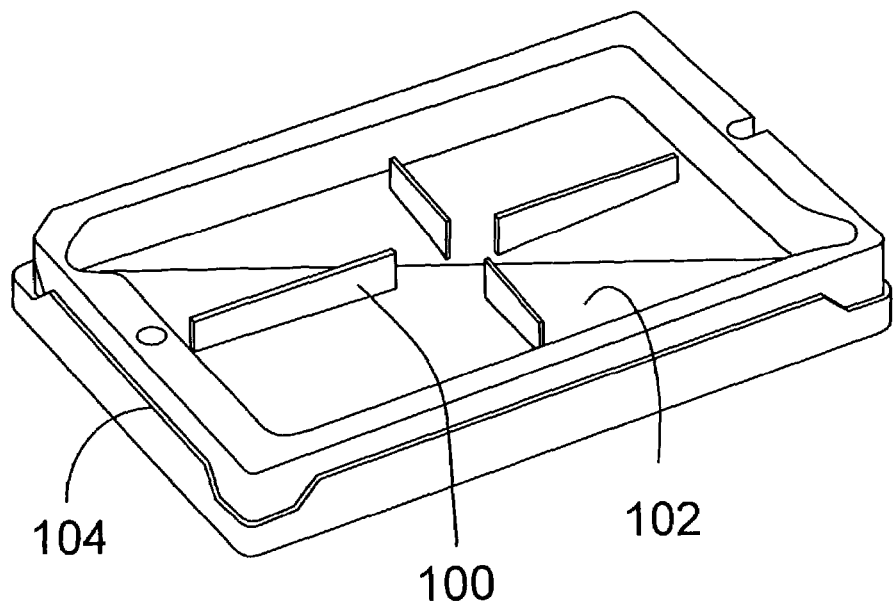
FIGS. 8A–D are a top down view of various alternative arrangements of the embodiment of FIG. 7.
Figure 8B:
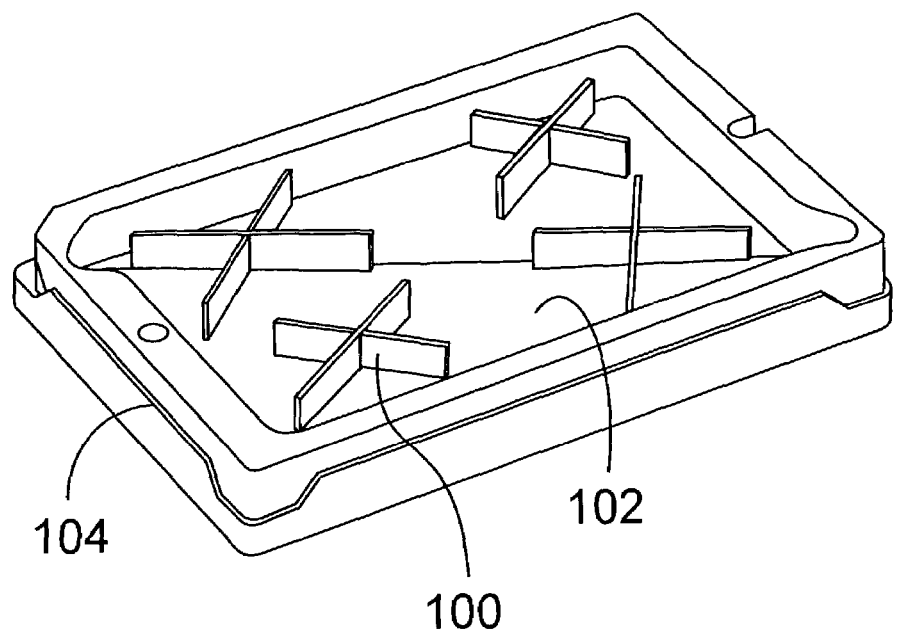
Figure 8C:
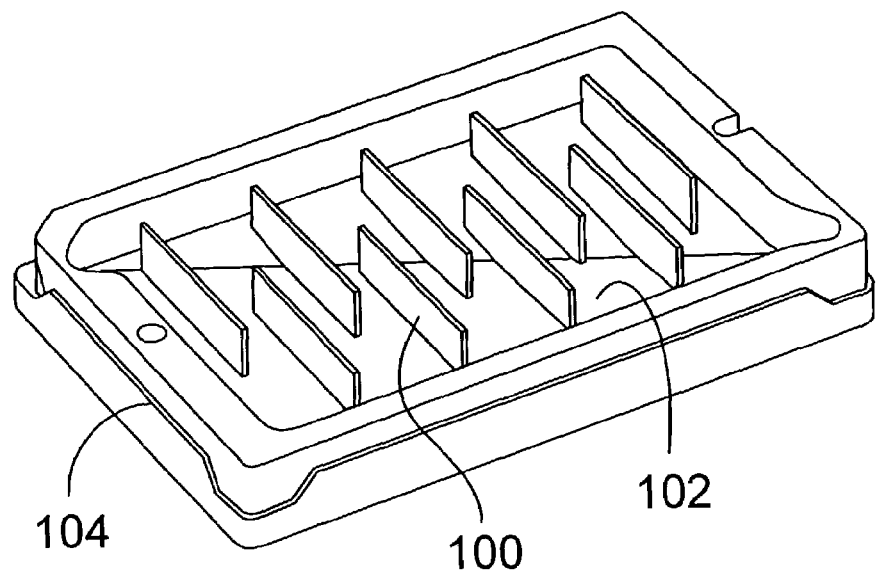
Figure 8D:
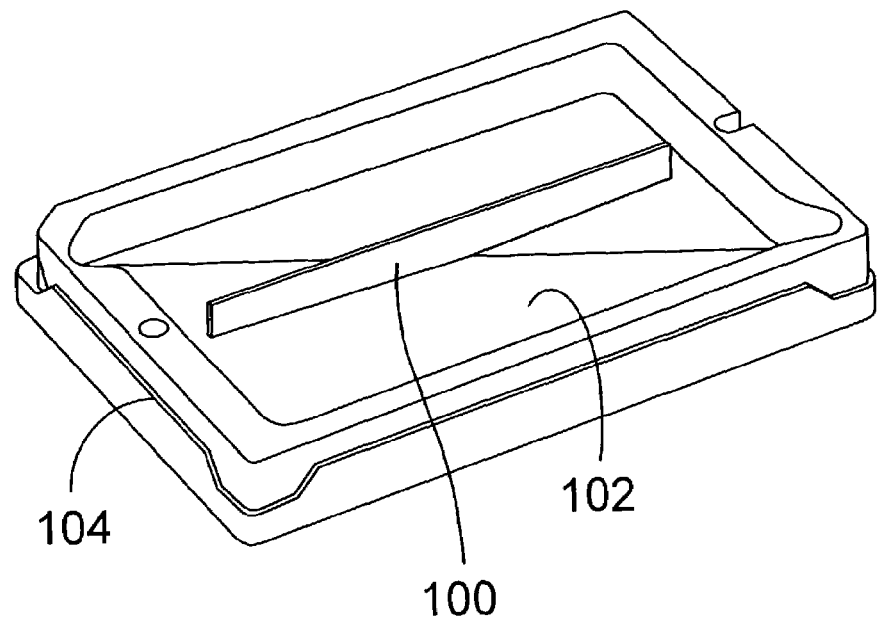

FIG. 8A shows an alternative arrangement of baffles in the embodiment of FIG. 7. In this Figure, straight baffles 100 are used instead of the wavy baffle design of FIG. 7. In FIG. 8B, the use of a series of repetitive baffles 100 is shown. Here, the baffles are shown as a series of "X" patterns spread across the feed tray bottom. FIG. 8C shows the use of a series of baffles 100 arranged in parallel and spaced part relationship to each other and each other baffle 100 extends out from the same side wall. In FIG. 8D is shown a single baffle that extend substantially the length of the feed tray.

Those baffles 100 that might extend across the inclined surface of the feed tray preferably have one or more through holes in them adjacent their bottom surface with the plate so as to allow for unimpeded flow along the incline. Alternatively, in those baffles that are separately formed, the baffles are made such that they only touch the tray bottom at a point away from the incline(s) so that fluid may flow under the baffle(s).

In another embodiment, the baffle(s) may be used in lieu of the posts or protrusions discussed above as the means for allowing one to remove excess liquid from the bottom of the cell plate during its removal from the feed tray. In this embodiment (not shown), the baffle(s) should be of a height similar to that of the post or protrusions discussed above. Further, the number of baffles used should sufficient to ensure that all wells of the cell plate receive sufficient force so as to knock off any droplets without disturbing the cells growing in the plate.

What is claimed is:

1. A multiwell test apparatus comprising a multiwell filter plate and a feeding tray to retain a liquid composition and to support the filter plate having a multiplicity of wells having an open top and bottom and a porous membrane attached to bottom, the feeding tray having an inclined support surface forming a lower area to which liquid can be introduced and from which liquid can be removed, and walls surrounding said inclined surface to enclose said inclined surface; and the multiwell filter plate comprising a multiplicity of wells extending from a plate, each of said wells comprising a member having an opening and extending from said plate and a porous membrane secured about said opening, the membranes of said wells positioned within a void volume of said feed plate, and said multiwell filter plate including a first access hole for introducing a liquid into said feeding tray and a second access hole for recovering liquid from said feeding tray.

2. A multiwell test apparatus comprising a multiwell filter plate and a feeding tray to retain a liquid composition and to support filter plate having a multiplicity of wells having an open top and bottom and a porous membrane attached to bottom, the feeding tray having an inclined support surface forming a lower area to which liquid can be introduced and from which liquid can be removed, the walls surrounding said inclined surface to enclose said inclined surface, and wherein said feeding tray includes an inclined support surface comprising a plurality of support surface subsections each inclined towards to a drainage path connected to said support surface subsections; and the multiwell filter plate comprising a multiplicity of wells extending from a plate, each of said wells comprising a member having an opening and extending from said plate and a porous membrane secured about said opening, the membranes of said wells positioned within a void volume of said feed plate, and said multiwell filter plate including a first access hole for introducing a liquid into said feeding tray and a second access hole for recovering liquid from said feeding tray.

3. A multiwell test apparatus comprising a multiwell filter plate and a feeding tray to retain a liquid composition and to support filter plate having a multiplicity of wells having an open top and bottom and a porous membrane attached to bottom, the feeding tray having an inclined support surface forming a lower area to which liquid can be introduced and from which liquid can be removed, the walls surrounding said inclined surface to enclose said inclined surface; and wherein said walls include outside surfaces configured to support a filter plate having a multiplicity of wells having an open top and an open bottom, a porous membrane is attached to the open bottom wherein each said porous membrane extends within a void volume above said support surface; and the multiwell filter plate comprising a multiplicity of wells extending from a plate, each of said wells comprising a member having an opening and extending from said plate and a porous membrane secured about said opening, the membranes of said wells positioned within a void volume of said feed plate, and said multiwell filter plate including a first access hole for introducing a liquid into said feeding tray and a second access hole for recovering liquid from said feeding tray.

4. A multiwell test apparatus comprising a multiwell filter plate and a feeding tray to retain a liquid composition and to support the filter plate having a multiplicity of wells having an open top and bottom and a porous membrane attached to bottom, the feeding tray having an inclined support surface forming a lower area to which liquid can be introduced and from which liquid can be removed, the walls surrounding said inclined surface to enclose said inclined surface, wherein said feeding tray includes an inclined support surface comprising a plurality of support surface subsections each inclined towards to a drainage path connected to said support surface subsections and wherein said walls include outside surfaces configured to support a filter plate having a multiplicity of wells having an open top and an open bottom, a porous membrane is attached to the open bottom wherein each said porous membrane extends within a void volume above said support surface; and the multiwell filter plate comprising a multiplicity of wells extending from a plate, each of said wells comprising a member having an opening and extending from said plate and a porous membrane secured about said opening, the membranes of said wells positioned within a void volume of said feed plate, and said multiwell filter plate including a first access hole for introducing a liquid into said feeding tray and a second access hole for recovering liquid from said feeding tray.

5. A multiwell test apparatus comprising a multiwell filter plate and a feeding tray to retain a liquid composition and to support the filter plate having a multiplicity of wells having an open top and bottom and a porous membrane attached to bottom, the feeding tray having an inclined support surface forming a lower area to which liquid can be introduced and from which liquid can be removed, the walls surrounding said inclined surface to enclose said inclined surface and wherein said feeding tray includes a multiplicity of protrusions extending from said support surface in a direction substantially the same direction as said walls extend from said support surface, said protrusions having a length which permits said protrusions to displace liquid within said walls; and the multiwell filter plate comprising a multiplicity of wells extending from a plate, each of said wells comprising a member having an opening and extending from said plate and a porous membrane secured about said opening, the membranes of said wells positioned within a void volume of said feed plate, and said multiwell filter plate including a first access hole for introducing a liquid into said feeding tray and a second access hole for recovering liquid from said feeding tray.

6. A multiwell test apparatus comprising a feeding tray to retain a liquid composition and to support a filter plate wherein the feeding tray has an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface; and a multiwell filter plate supported by the walls of said feeding tray, the multiwell filter plate comprising a multiplicity of wells extending from a plate, each of said wells comprising (a) a member having an opening and extending from said plate and (b) a porous membrane secured about said opening, the membranes of said wells positioned within a void volume of said feed plate, and said multiwell filter plate including a first access hole for introducing a liquid into said feeding tray and a second access hole for recovering liquid from said feeding tray.

7. A multiwell test apparatus comprising a feeding tray to retain a liquid composition and to support a filter plate wherein the feeding tray has an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface and wherein said feeding tray includes an inclined support surface comprising a plurality of support surface subsections each inclined towards to a drainage path connected to said support surface subsections; and a multiwell filter plate supported by the walls of said feeding tray, the multiwell filter plate comprising a multiplicity of wells extending from a plate, each of said wells comprising (a) a member having an opening and extending from said plate and (b) a porous membrane secured about said opening, the membranes of said wells positioned within a void volume of said feed plate, and said multiwell filter plate including a first access hole for introducing a liquid into said feeding tray and a second access hole for recovering liquid from said feeding tray.

8. A multiwell test apparatus comprising a feeding tray to retain a liquid composition and to support a filter plate wherein the feeding tray has an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface and wherein the feeding tray walls include outside surfaces configured to support a filter plate having a multiplicity of wells having an open top and an open bottom, a porous membrane is attached to the open bottom wherein each said porous membrane extends within a void volume above said support surface and a multiwell filter plate supported by the walls of said feeding tray, the multiwell filter plate comprising a multiplicity of wells extending from a plate, each of said wells comprising (a) a member having an opening and extending from said plate and (b) a porous membrane secured about said opening, the membranes of said wells positioned within a void volume of said feed plate, and said multiwell filter plate including a first access hole for introducing a liquid into said feeding tray and a second access hole for recovering liquid from said feeding tray.

9. A multiwell test apparatus comprising a feeding tray to retain a liquid composition and to support a filter plate wherein the feeding tray has an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface, said feeding tray includes an inclined support surface comprising a plurality of support surface subsections each inclined towards to a drainage path connected to said support surface subsections and wherein the feeding tray walls include outside surfaces configured to support a filter plate having a multiplicity of wells having an open top and an open bottom, a porous membrane is attached to the open bottom wherein each said porous membrane extends within a void volume above said support surface; and a multiwell filter plate supported by the walls of said feeding tray, the multiwell filter plate comprising a multiplicity of wells extending from a plate, each of said wells comprising (a) a member having an opening and extending from said plate and (b) a porous membrane secured about said opening, the membranes of said wells positioned within a void volume of said feed plate, and said multiwell filter plate including a first access hole for introducing a liquid into said feeding tray and a second access hole for recovering liquid from said feeding tray.

10. A multiwell test apparatus comprising a feeding tray to retain a liquid composition and to support a filter plate wherein the feeding tray has an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface and wherein said feeding tray includes a multiplicity of protrusions extending from said support surface in a direction substantially the same direction as said walls extend from said support surface, said protrusions having a length which permits said protrusions to displace liquid within said walls; and a multiwell filter plate supported by the walls of said feeding tray, the multiwell filter plate comprising a multiplicity of wells extending from a plate, each of said wells comprising (a) a member having an opening and extending from said plate and (b) a porous membrane secured about said opening, the membranes of said wells positioned within a void volume of said feed plate, and said multiwell filter plate including a first access hole for introducing a liquid into said feeding tray and a second access hole for recovering liquid from said feeding tray.

* * * * *